(12) United States Patent
Gilad et al.

(10) Patent No.: US 9,585,852 B2
(45) Date of Patent: *Mar. 7, 2017

(54) AGMATINE CONTAINING DIETARY SUPPLEMENTS, NUTRACEUTICALS AND FOODS

(71) Applicants: Gad Gilad, Los Angeles, CA (US); Varda Gilad, Los Angeles, CA (US)

(72) Inventors: Gad Gilad, Los Angeles, CA (US); Varda Gilad, Los Angeles, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 14/557,217

(22) Filed: Dec. 1, 2014

(65) Prior Publication Data
US 2015/0086523 A1 Mar. 26, 2015

Related U.S. Application Data

(63) Continuation of application No. 12/698,042, filed on Feb. 1, 2010, now Pat. No. 8,916,612, which is a continuation-in-part of application No. PCT/US2009/054013, filed on Aug. 17, 2009.

(60) Provisional application No. 61/136,531, filed on Sep. 11, 2008.

(51) Int. Cl.
| | | |
|---|---|---|
| A61K 31/155 | (2006.01) |
| C07C 279/12 | (2006.01) |
| A23L 2/52 | (2006.01) |
| A23C 9/13 | (2006.01) |
| A61K 45/06 | (2006.01) |
| A61P 25/02 | (2006.01) |
| A23L 1/305 | (2006.01) |
| A23K 1/16 | (2006.01) |

(52) U.S. Cl.
CPC .............. *A61K 31/155* (2013.01); *A23C 9/13* (2013.01); *A23K 20/142* (2016.05); *A23K 20/147* (2016.05); *A23L 2/52* (2013.01); *A23L 33/10* (2016.08); *A23L 33/17* (2016.08); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,077,313 A | 12/1991 | Lubec |
| 6,150,419 A | 11/2000 | Fairbanks et al. |
| 6,887,493 B2 | 5/2005 | Shefer et al. |
| 7,122,213 B2 | 10/2006 | Anno et al. |
| 7,138,386 B2 | 11/2006 | Nakagiri et al. |
| 7,273,607 B2 | 9/2007 | Schakel et al. |
| 7,816,407 B2 | 10/2010 | Crooks |
| 8,916,612 B2 * | 12/2014 | Gilad et al. ............ A61K 31/15 |
| 2002/0065323 A1 | 5/2002 | Crooks et al. |
| 2003/0152629 A1 | 8/2003 | Shefer |
| 2005/0096369 A1 | 5/2005 | Hoang |

FOREIGN PATENT DOCUMENTS

WO 2010/030470 A1 3/2010

OTHER PUBLICATIONS

Man Blueprint [retrieved on Sep. 16, 2009] Retrieved from internet <URL: http://web.archive.org/web/20070525034636/http://www.milehighmuscle.com/manbl80ca.html> published on May 25, 2007 as per Wayback Engine , 5 pages.
Man Body Octane [retrieved on Sep. 16, 2009] Retrieved from Internet <URL: http://web.archive.org/web/20070629181836/http://www.bodybuilding.com/store/man/body.html> published on Jun. 29, 2007 as per Wayback Engine , 5 pages.
Scorch <URL: http://web.archive.org/web/20070622191000/www.goendurance.com/p1562_Scorch_MAN.html> published on Aug. 23, 2007 as per Wayback engine , 7 pages.
Silveira T.J. et al., "Profile and levels of bioactive amines in instant coffee" Food Composition and Analysis (2007), vol. 20, p. 451-457.
Moinard C et al., "Polyamines: metabolism and implications in human diseases" Clinical Nutrition (2005) vol. 24, p. 184-197.
PCT International Searching Authority, International Search Report and Written Opinion of the International Searching Authority, Mar. 29, 2011.
Kalantar-Zadeh et al., "Association Among SF36 Quality of Life Measures and Nutrition, Hospitalization, and Mortality in Hemodialysis"; J Am Soc Nephrol 12: 2797-2806, 2001.
Berenholz et al., "Agmatine treatment and vein graft reconstruction enhanced recovery after experiemntal facial nerve injury"; Journal of the Peripheral Nervous System 10:319-328 (2005).

* cited by examiner

*Primary Examiner* — Chris R Tate
*Assistant Examiner* — Aaron J Kosar
(74) *Attorney, Agent, or Firm* — Trojan Law Offices

(57) ABSTRACT

The invention is dietary supplements, nutraceutical compositions, medical foods, and animal feeds that have cytoprotective (cell and tissue protection) and health promoting effects. The compositions contain a high dose range of agmatine and nutraceutical acceptable salts thereof as dietary fortification for providing effective long-term cytoprotection and affording for soft stool. The compositions may contain agmatine alone or in combination with other dietary ingredients having health promoting effects. The compositions can be prepared with dietary accepted excipients and compatible forms of carriers, including but not limited to, powders, tablets, capsules, controlled release carriers, lozenges and chewable preparations, liquid suspensions, suspensions in an edible supporting matrix or foodstuff and oral rehydration solutions, to enable consumption of said compositions.

19 Claims, 3 Drawing Sheets

AGMATINE CONTAINING DIETARY SUPPLEMENTS, NUTRACEUTICALS AND FOODS

CROSS REFERENCE TO RELATED APPLICATIONS

The present application is a continuation of, and claims priority to U.S. patent application Ser. No. 12/698,042, filed on Feb. 1, 2010, which is continuation-in-part of, and claims priority to, International Patent Application Number PCT/US2009/054013, filed on Aug. 17, 2009, which claims priority to U.S. Provisional Application No. 61/136,531, filed on Sep. 11, 2008, which are all hereby expressly incorporated by reference as though set herein in their entirety.

FIELD OF THE INVENTION

The present invention relates to compositions of matter in the field of dietary ingredients and nutraceuticals, dietary supplements, medical foods and foods and animal feeds which incorporate them. More in particular, the present invention is related to dietary supplement and foods which incorporate high content of agmatine or nutraceutical acceptable salts thereof for safe and long-term use as cytoprotective ingredients and their formulations in combination with other traditional dietary ingredients (e.g., fibers, probiotics, vitamins, minerals, fatty acids, amino acids, phytonutrients, vitamins, and mixtures thereof) having health promoting effects on several bodily systems. The present invention is also directed at nutrition of animals in need thereof, by administering feed containing the above dietary ingredient formulations.

BACKGROUND OF THE INVENTION

Selective nutrients, such as amino acids are recommended at specified daily dosage to sustain healthy function of bodily systems. The term nutraceutical was coined in the early 1990s by Stephen de Felice, founder and chairman of the Foundation for Innovation in Medicine, to define a food or part of a food including compounds found in food and dietary supplements in food dosage forms that have a health benefit. Further of his assertions though, including the prevention and treatment of disease are unacceptable by the various regulatory health authorities.

Agmatine as a Dietary Ingredient:

Agmatine [$(NH_2(CH_2)_4NH_2C(NH=)NH$], a metabolite of the amino acid arginine, was discovered by Albrecht Kossel in 1910. It is a naturally occurring molecule ubiquitously found in nature, which is biosynthesized by decarboxylation of the amino acid arginine (itself a dietary ingredient), thus known as decarboxylated arginine (see Raasch W, et al., J Pharmacol, (2001) 133:755-780, for comprehensive summary). Agmatine is found in low amounts in many foodstuff derived from plants, fish, with levels as-high-as 200 to 650 mg/kg found in certain fish, and animal products. Importantly, normal agmatine fecal concentrations are the highest among amines, at 14.42 µmol/g dry weight. Microbial production of agmatine, therefore, is considered important source for absorption of agmatine into the body by the mucosal lining of the large intestine (Haenisch B, et al., Am J Physiol Gastrointest Liver Physiol, (2008) November; 295(5): G1104-10).

Agmatine Effects on Bodily Systems:

Ample evidence from laboratory animal studies indicates that treatment with agmatine exerts beneficial health promoting effects on various tissues and bodily functions including mild antihypertensive, cardioprotective and nephroprotective effects. Of specific interest, is the substantial body of evidence demonstrating the beneficial effects of agmatine on the nervous system. These include neuroprotection (Gilad G M, et al., Life Sci, (1995) 58:PL41-PL46; Gilad G M and Gilad V H, Neurosci Lett, (2000) 296:97-100; Gilad G M and Gilad V H, U.S. Pat. No. 5,677,349, Oct. 14, 1997), neuropathic pain-reducing effects (Fairbanks C A et al., U.S. Pat. No. 6,150,419, Nov. 21, 2000), anticonvulsive effects, and anti-anxiety and anti-depressive effects (Fiori L M and Turecki G, J Psychiatry Neurosci (2008) 33:102-10). Enhanced glucose metabolism associated with increased insulin release, and reduced catecholamine release associated with mild reduction in blood pressure and heart rate, are additional beneficial effects of agmatine that may be contributory to its salutary effects on the nervous system. Furthermore, while agmatine biosynthesis (by arginine decarboxylation) in the nervous system is normally very low, it is greatly increased in response to injury (Raasch W, et al., J Pharmacol, (2001) 133:755-780 (p. 764)), thus further implicating agmatine in neuroprotection. Additionally, while agmatine was long known to stimulate proliferation of certain blood born cell types (e.g., thymocytes and lymphocytes), it was found to be a cytotactic compound, preventing cell proliferation of various other cell types (including endothelial cells and astrocytes, as well as various cancer cells) (Gilad G M, et al., Life Sci, (1995) 58:PL41-PL46; Regunathan S and Reis D J, U.S. Pat. No. 5,574,059, Nov. 12, 1996; Fahl W E and Kink J, U.S. Pat. No. 7,045,550, May 16, 2006). Several other patents cover topical (not enteric) application of agmatine for wound healing and cytotactic anti-proliferation effects and therefore, are not related to this application (Raisfeld I H, U.S. Pat. No. 4,507,321, Mar. 26, 1985; Wohlrab J, International Publication No. WO/2003/092668, November 143, 2003; Oblong J E, et al., International Publication No. WO/2004/078157, Sep. 16, 2004).

Agmatine Absorption, Distribution, and Metabolism:

Animal studies demonstrated that agmatine is absorbed by the gastrointestinal tract and distributed in the body, and that it crosses the blood-brain barrier (Haenisch B, et al., Am J Physiol Gastrointest Liver Physiol, (2008) November; 295(5):G1104-10), for comprehensive summary). In the intestinal tract, agmatine can exert diamine oxidase inhibition, which may lead to increased histamine and thus may be unwanted, but at the same time it can lead to favorable accumulation of polyamines, known growth factors of intestinal mucosa. In the body, agmatine is principally metabolized into urea, a known dietary ingredient in ruminant feed, and putrescine, the diamine precursor of polyamines, which are essential for cell growth and viability in general and specifically so for neuroprotection. Otherwise, agmatine can be oxidized and secreted by the kidneys, but this is probably negligible. Agmatine can moderately increase glomerular filtration rate and natriuresis (increased sodium excretion), which may be desired or unwanted depending on health status. Additionally, it can increase gastric acid secretion, which may increase incidence of stress-induced ulcers in laboratory rats. No toxic effects, however, were observed in several species including mice, rats, dogs, calves and monkeys during or after oral intake of agmatine at a variable dose ranges and regimens (see Example II). Taken together, the evidence indicates that dietary agmatine can be considered safe at a daily dose range of about 200-500 mg/kg/day in small animals (e.g., rats and mice) and at lower doses in larger animals with corresponding lower metabolic rates (e.g., up to about 20-80 mg/kg/day in dogs and 10-40 mg/kg/day in horses).

Agmatine Mechanisms of Action:

The cytoprotective mechanism of agmatine action—defined as mechanism promoting cellular resilience and cell survival capabilities—is postulated to be multifunctional. Laboratory studies with experimental animals implicate agmatine in a range of molecular targets important for cytoprotection (Raasch W, et al., J Pharmacol, (2001) 133: 755-780). These include: modulation of several neurotransmitter receptors and receptor ionophores (e.g., nicotine, NMDA, imidazoline, and alpha 2-adrenoceptors); blockage of key ionic channels (e.g., ATP-sensitive K+ channels and voltage-gated Ca++ channels); inhibition of nitric oxide (NO) synthase and thus, reduced NO production; inhibition of protein ADP-ribosylation and thus, interfering with cell signaling; inhibition of matrix metalloproteases (MMPs), enzymes implicated in nerve cell death and neuropathic pain; and, inhibition of advanced glycation end (AGE)-product formation, which is a process involved in the pathology of diabetes and neurodegenerative diseases (Lubec G, U.S. Pat. No. 5,077,313, Dec. 31, 1991). The above outlined cytoprotective mechanisms attributed to agmatine underlie its neuroprotective, cardioprotective, nephroprotective, and glycemic control (sometime referred to as glucoprotective) effects. Agmatine acts at multiple molecular targets involved in promoting healthy bodily functions.

Agmatine as a Nutraceutical Cytoprotective Dietary Ingredient:

Although the above references disclose that many of the effects, mechanisms, and metabolism of agmatine are known, the prior art is devoid of any references that disclose that agmatine may be used as a fortifying measure adding to tissue resilience against future insults, thus presenting a beneficial cytoprotective nutraceutical supplement to the diet of a human or animal. However, there are references that disclose what levels of agmatine would be safe to consume and that agmatine may be a beneficial ingredient to a topical application, as discussed above, or for treatment of specific existing disorders. For example, the long known mild hypoglycemic effects of agmatine in experimental animal studies (Raasch W, et al., J Pharmacol, (2001) 133:755-780) and earlier reports on its oral use in diabetics in Oskar Minkowski's clinic in Breslau, Germany, already in the late 1920s (Kleiner I S, Clin. Chem, (1959) 5:79), are evidence for its safety and efficacy as a dietary ingredient by promoting normal glucose metabolism, thus providing glucoprotection in diabetes. Moreover, in humans, agmatine is present in the mucus secreting cells of the stomach and is postulated to play role in acid protection of the stomach, (i.e., gastroprotective effect) (Steer H, Anat Rec, (2009) 292:79-86). Furthermore, a recent clinical study demonstrated safety and suggested efficacy of dietary agmatine in degenerative lumbar spine disorders causing nerve root compression (this report did not disclose agmatine by name: Keynan O, Gilad V H, Dekel S, Gilad G M, An open label phase I dose escalating, non randomized study to assess the safety of a food supplement in patients with lumbar radiculopathy, Israel Spine Soc 8th Ann Meet (Abst), Eilat, Israel, 2007), thus indicating its neuroprotective effects in human. Furthermore, several internet sites (e.g., Man Sports BLUE-PRINT http://www.discountanabolics.com/p/MF-006) tout agmatine containing supplements at dose ranges of up to 1 grams per day for body building. However, as will be discussed below in the Description of the Present Invention and in Examples I-III, it is disclosed for the first time that agmatine can be safely taken in the diet at an unpredictably high daily dose range of 1.780-3.560 grams as a long-term regimen (years). Furthermore, agmatine is now disclosed for the first time as an efficacious cytoprotective measure when used to fortify the diet as an ingredient in dietary supplements prior to bodily trauma.

The prior art is silent regarding dietary supplements, nutraceuticals, medical foods, and processed food compositions containing agmatine as a dietary ingredient at the indicated high, long-term daily dosage of 1.780-3.560 grams, or for providing preventive cytoprotection. Importantly, this stands in obvious contrast to the proposed pharmaceutical uses of agmatine as a drug treatment for various preexisting conditions, some of which are discussed herein.

The present invention, therefore, provides effective, useful, and novel nutraceuticals, dietary supplements, medical foods, and food compositions incorporating an effective high dosage amount of agmatine, and nutraceutical acceptable salts thereof as a safe and long-term daily measure for preventive cytoprotection, such as defined by Mueller C. (Nutrition 15:249-251, 1999). Accordingly, the essence of the present invention is cytoprotective high dosage amount of dietary agmatine as a safe preventive measure directed at promoting cellular resilience and cell survival capabilities. This newly discovered usage of dietary agmatine could not have been anticipated or predicted and was not previously taught, suggested, or disclosed by the prior art. Thus, the present invention fills a need not currently available in the market place.

Citation of any document herein is not intended as an admission that such document is pertinent prior art, or considered material to the patentability of any claim of the present application. Any statement as to content or a date of any document is based on the information available to the applicants at the time of filing and does not constitute an admission as to the correctness of such a statement.

SUMMARY OF THE INVENTION

The present invention seeks to provide dietary supplements and nutraceutical compositions containing agmatine and nutraceutical acceptable salts thereof at a newly discovered high dosage range to safely fortify the diet as a cytoprotective measure in humans and animals.

The other dietary ingredients consist of an effective amount of one or more of dietary ingredients selected from the traditional group of minerals, including, but not limited to, magnesium, selenium, zinc, chromium; fatty acids, including, but not limited to, alpha- and gamma-linolenic acid, thioctic (alpha-lipoic) acid, omega-3 family of unsaturated fatty acids; amino acids and metabolites, including, but not limited to, creatine, N-acetyl carnitine, melatonin; phytonutrients, including, but not limited to, carotenoid derivatives (e.g., the xanthophyll type such as zeaxanthin and tetraterpenes such as beta-carotene), phytosterols, flavonoids, Isoflavones; vitamins and coenzymes, including, but not limited to, vitamin A, vitamin C, vitamin E, coenzyme Q10; and mixtures thereof The invention also provides for a nutraceutical medical food composition containing the dietary ingredient agmatine comprising: (a) an effective cytoprotective amount of agmatine consisted of nutraceutical acceptable salts thereof; and (b) an effective formulation of clinically accepted medical food, which contains an effective cytoprotective amount of agmatine consisted of nutraceutical acceptable salts thereof.

Further, the invention is directed at providing processed food and beverage compositions incorporating effective cytoprotective amounts of agmatine consisted of nutraceutical acceptable salts thereof in accepted categories of functional foods, including, but not limited to, cereals and fermented dairy foods, and beverages, including, but not limited to, teas, juices, water, and alcoholic beverages, which are fortified with health promoting ingredients including, but not limited to, fibers, probiotics, vitamins and coenzymes, minerals, fatty acids, amino acids and metabolites thereof, phytonutrients, and mixtures thereof.

In addition the invention is directed at providing nutrition of animals in need by administering feed to said animals of a composition comprising: (a) an effective amount of agmatine consisted of nutraceutical acceptable salts thereof, and (b) an effective amount of one or more of dietary ingredients selected from the traditional group of minerals, including, but not limited to, magnesium, selenium, zinc, chromium; fatty acids, including, but not limited to, alpha- and gamma-linolenic acid, thioctic (alpha-lipoic) acid, omega-3 family of unsaturated fatty acids; amino acids and metabolites, including, but not limited to, creatine, N-acetyl carnitine, melatonin, methylsulfonylmethane (MSM); phytonutrients, including, but not limited to, carotenoid derivatives (e.g., the xanthophyll type such as zeaxanthin and tetraterpenes such as beta-carotene), phytosterols, flavonoids, Isoflavones; vitamins and coenzymes, including, but not limited to, vitamin A, vitamin C, vitamin E, coenzyme Q10; and mixtures thereof.

The present invention is further directed to provide the dietary supplement an nutraceutical formulations aforementioned in the form of powders, tablets, capsules, soft gelatin capsules, controlled release capsules and tablets, lozenges and chewable preparations, liquid suspensions, suspensions in an edible supporting matrix or foodstuff and oral rehydration solutions, to enable consumption of effective cytoprotective amount of nutraceutical acceptable agmatine salt, such as agmatine sulfate, at a daily dose range of between 1.780 grams and up to 3.560 grams. This range is based on administration to a human weighing 60 to 70 kg.

Other advantages will become apparent as further described below in the preferred embodiments of the present invention.

Advantages of the Invention a. A primary advantage of the present invention is to provide nutraceutical and dietary supplement compositions incorporating high amounts of agmatine and nutraceutical acceptable salts thereof as cytoprotective health promoting dietary supplements for long-term consumption at a high dose range of 1.780-3.560 grams/day in humans.

b. Another important advantage of the present invention is to provide dietary supplement formulations containing high cytoprotective amounts of agmatine and nutraceutical acceptable salts thereof in combination with other traditional dietary ingredients, including, minerals, fatty acids, amino acids and metabolites thereof, phytonutrients, vitamins and coenzymes, having health promoting effects.

c. An additional advantage of the present invention is to provide the dietary supplement formulations described in (a) and (b) above in the form of powders, tablets, capsules, soft gelatin capsules, controlled release capsules and tablets, lozenges and chewable preparations, liquid suspensions, suspension in an edible supporting matrix or foodstuff and oral rehydration solutions, to enable consumption of effective agmatine dosage.

d. A further important advantage of the present invention is to provide nutraceutical compositions incorporating high cytoprotective amounts agmatine and nutraceutical acceptable salts thereof as medical foods formulated to be consumed or administered orally for dietary management of specific health-related conditions.

e. Another advantage of the present invention is to provide processed food and beverage compositions incorporating high cytoprotective amounts of agmatine and nutraceutical acceptable salts thereof in accepted categories of functional foods, including, but not limited to, cereals and fermented dairy foods, and beverages, including, but not limited to, teas, juices, water, and alcoholic beverages, which are fortified with health promoting ingredients including, but not limited to, fibers, probiotics, vitamins, coenzymes, minerals, fatty acids, amino acids and metabolites thereof, phytonutrients, and mixtures thereof.

f. Another advantage of the present invention is to provide animal feed containing dietary supplements incorporating high cytoprotective amounts of agmatine and nutraceutical acceptable salts thereof as a safe long-term cytoprotective measure to animals in need thereof.

g. An additional important advantage of the present invention is to provide nutraceutical and dietary supplement compositions incorporating the high 1.780-3.560 grams/day dose range of agmatine and nutraceutical acceptable salts thereof for affording soft stool in humans.

Further aspects of the invention will become apparent from consideration of the ensuing description of preferred embodiments of the invention. A person skilled in the art will realize that other embodiments of the invention are possible and that the details of the invention can be modified in a number of respects, all without departing from the inventive concept. Thus, the following description is to be regarded as illustrative in nature and not restrictive.

DESCRIPTION OF THE PREFERRED EMBODIMENTS

Figure 1:
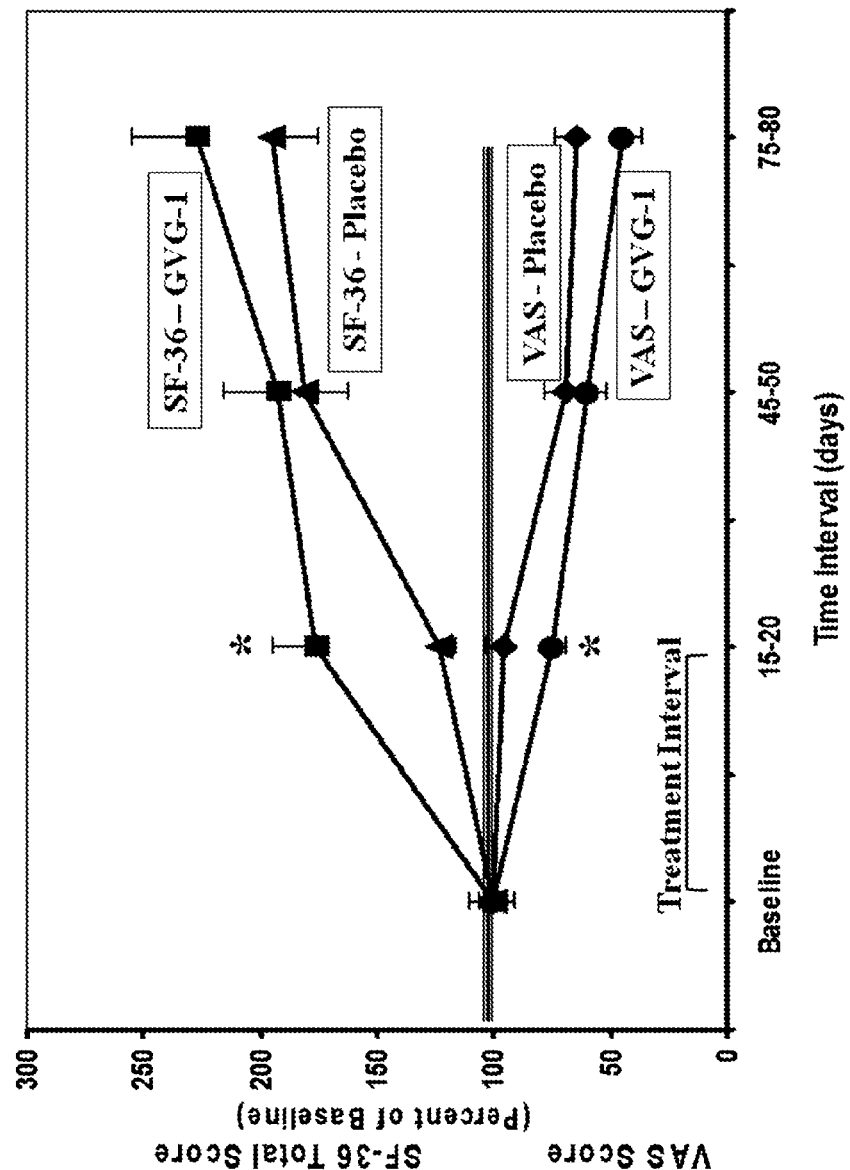
FIG. 1 shows a graph displaying changes in pain in accordance with the present invention.

In the following detailed description of various embodiments of the invention, numerous specific details are set forth in order to provide a thorough understanding of various aspects of one or more embodiments of the invention. However, one or more embodiments of the invention may be practiced without these specific details. In other instances, well-known methods, procedures, and/or components have not been described in detail so as not to unnecessarily obscure aspects of embodiments of the invention.

In the following description, certain terminology is used to describe certain features of one or more embodiments of the invention. For instance:

"Nutraceutical acceptable salts" refers to water soluble compounds composed of cations (such as agmatine) bound to inorganic or organic acids, thus readily available in body fluids, which are known to be safe and to exert health promoting effect upon consumption.

"Metabolites" refers to the products of biochemical transformations of chemical compounds by enzymes in living organisms.

"Vitamin" refers to a chemical compound needed for proper bodily functions, which cannot be made by the body itself and is usually obtain through food.

"Coenzymes" refers to non-protein chemical compounds that are bound to enzymes and are required for the biological activity of the enzymes, thus assisting in biochemical transformations.

"Fatty Acids" refers to carboxylic acids consisted of a short or long usually un-branched aliphatic chain of carbons that is either saturated or unsaturated (containing double or single carbon-carbon bond, respectively), derived from breakdown of animal or vegetable fat, oil, or wax.

"Phytonutrients" refers to classes of natural organic substances that are found in plants and thought to promote health, which include: carotenoids, flavonoids (Polyphenols) and isoflavones (Phytoestrogens), inositol phosphates (Phytates), lignans (Phytoestrogens), isothiocyanates and indoles, phenols and cyclic Compounds, saponins, sulfides and thiols, and terpenes.

"Probiotics" refers to dietary supplements consisted of live microorganisms usually lactic acid bacteria and bifidobacteria, but also certain yeasts and bacilli, which in adequate amounts confer health benefits on the host.

"Excipient" refers to an inactive substance used as a carrier to enable proper delivery and absorption of the active ingredients of dietary supplements and medications.

"Medical Food" refers to food formulated for enteric administration under physician supervision and intended for the specific dietary management of a disease or condition for which distinctive nutritional requirements are established by medical evaluation.

"Processed Food" refers to any food that is changed from its natural, raw state, but often more narrowly defined as a food which has been chemically altered through additives such as flavors, flavor enhancers, binders, colors, fillers, preservatives, stabilizers, emulsifiers, etc., or which has been manufactured through combination or other methods.

"Processed Beverage" refers to any one of various liquids for drinking that is changed from its natural, raw state (e.g., juices, milk, etc.), but often more narrowly defined as a drink which has been chemically altered through additives such as flavors, flavor enhancers, colors, preservatives, stabilizers, emulsifiers, etc., or which has been manufactured through combination or other methods.

"Cytoprotection" refers to protection of cells from trauma, injury and lethal agents by fortifying measures (such as agmatine treatment) directed at activation of biochemical and molecular mechanisms which promote cellular resilience and cell survival capabilities.

Of the disclosed dietary supplements and nutraceuticals, the preferred composition of the present invention contains the high effective amount of dietary agmatine as a cytoprotective ingredient consisted of nutraceutical acceptable salts thereof. The rational for the preferred dietary supplements and nutraceutical compositions containing high agmatine concentrations is based on substantial solid scientific evidence that shows safety and specific use efficacy in both animal and human studies. Evidence, derived mainly from animal studies, shows that agmatine treatment exerts general protection of cells and tissues from damage as demonstrated by the following: effective neuroprotection associated with accelerated nerve regeneration and functional recovery; reduced allodynia (increased pain sensitivity characteristic of various neuropathies) after traumatic nerve injury; increased kidney glomerular filtration rate and natriuresis (increased sodium excretion); effective nephro-protection; and mild antihypertensive and mild reduction in heart rate, both of which result from reduced catecholamine release and normalize endothelial-dependent relaxation, and effective cardio-protection. Additionally, agmatine treatment imparts glycemic control (i.e., glucoprotection), which is cardinal for general tissue preservation, by both increasing insulin release and cellular glucose uptake, thus lowering plasma glucose. Furthermore, agmatine treatment results in reduced anxiety- and depressive-associated behavior in response to stressful conditions. Human studies indicate that agmatine may produce gastroprotective effect via acid protection of the stomach. Additional to the anti-neuropathic effect in human, agmatine sulfate treatment may result in soft stool or mild diarrhea—an effect welcomed by those who suffer from constipation due to painkillers (especially opioid medications).

To produce its cytoprotective and pain reducing effects, agmatine interacts with multiple molecular mechanisms, which include: several neurotransmitter receptors (e.g., NMDA receptors, nicotinic receptors and alpha 2-adrenoceptors); key ionic channels (e.g., ATP-sensitive $K^+$ channels and voltage-gated $Ca^{++}$ channels); NO synthesis; protein ADP-ribosylation; matrix metalloproteases (MMPs); and advanced glycation end (AGE)-product formation.

Agmatine is uniquely poised as a single dietary ingredient with multiple sites of action important for cytoprotection and, thus, is advantageous as an efficacious cytoprotective ingredient when used at the newly discovered high daily dosage to fortify the diet.

The preferred composition of the present invention contains an effective amount of dietary agmatine as a cytoprotective ingredient in the form of nutraceutical acceptable salts. Practically all prior art and the examples described herein were performed using the sulfate salt of agmatine [$(NH_2)(CH_2)_4NH(NH=)CNH_2.H_2SO_4$, CAS No. 2482-00-0]. But the present invention provides for the use of agmatine in the form of nutraceutical acceptable salts derived from inorganic or organic acids which include, but are not limited to, acetate, adipate, alginate, citrate, aspartate, benzoate, benzenesulfonate, sulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmitate, pectinate, persulfate, 2-phenylpropionate, picrate, pivalate, propionate, succinate, tartrate, thiocyanate, tosylate, mesylate, and undecanoate. Furthermore, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides, such as benzyl and phenethyl bromides, and other agents. Water- or oil-soluble or dispersible products are thereby obtained.

Other dietary supplements and nutraceutical formulations comprise an effective amount of agmatine consisted of nutraceutical acceptable salts thereof and an effective amount of one or more of dietary ingredients selected from the traditional group of minerals, including, but not limited to, magnesium, selenium, zinc, chromium (typically incorporated as their salt forms); fatty acids, including, but not limited to; alpha- and gamma-linolenic acid, thioctic (alpha-lipoic) acid, omega-3 family of unsaturated fatty acids; amino acids and metabolites, including, but not limited to, creatine, N-acetyl carnithine, melatonin; phytonutrients, including, but not limited to: carotenoid derivatives (e.g., the xanthophyll type such as zeaxanthin and tetraterpenes such as beta-carotene), phytosterols, flavonoids, Isoflavones; vitamins and coenzymes, including, but not limited to, vitamin A, vitamin C, vitamin E, coenzyme Q10; and mixtures thereof.

The amount of the nutraceuticals to be used in dosage forms is preferably an amount that is considered safe for human consumption and approved by the acceptable guidelines promulgated by the US Food and Drug Administration. For humans, the daily dose range for agmatine is not established. However, a safe daily dose range is available based on the cited animal experiments and the present human clinical studies. Animal studies indicate that dietary agmatine can be considered safe at a daily dose range of about 200-500 mg/kg/day in small animals (e.g., rats and mice) (see Example II) and at lower doses in larger animals with corresponding lower metabolic rates (e.g., up to about 20-80 mg/kg/day in dogs and 10-40 mg/kg/day in horses). For humans, the recommended daily dose to enable consumption of effective cytoprotective amount of nutraceutical acceptable agmatine salt, such as agmatine sulfate is at the range of between 1780 mg/day and up to 3560 mg/day. This range is based on administration to a human weighing 60 to 70 kg (see Example I).

This recommendation is supported by recent clinical trials (Keynan O, Mirovsky Y, Dekel S, Gilad V H, Gilad G M. Safety and efficacy of dietary agmatine sulfate in lumbar disc-associated radiculopathy. An open label, dose-escalating study followed by a randomized, double-blind, placebo-controlled trial. Pain Med, (2010) in press). These studies demonstrated for the first time that dietary agmatine sulfate is safe and efficacious when taken at a high dose range of up to 3.560 grams per day for duration of up to 2 years (Example I). In the randomized, double-blind, placebo-controlled (RCT) trial, eligible participants received either placebo or agmatine sulfate (2.670 g/day for 14 days) in a double-blind fashion. Analysis was performed on 30 participants in the placebo and 31 in the agmatine sulfate arm. Primary outcome measures including neuropathic pain and health-related quality of life demonstrated a more pronounced improvement in the agmatine sulfate-treated group. Secondary outcomes included assessments of safety and tolerability. Importantly, no adverse effects were noted during the course of the trial. While the severity of pain symptoms and general health status improved with time in both placebo and agmatine sulfate-treated groups, the improvements were more pronounced in the agmatine sulfate-treated group. As illustrated in the graph (1) in FIG. 1, statistically significant enhanced improvements in the agmatine sulfate-treated group as compared to placebo were noted at the follow-up interval immediately after treatment termination (15-20 day) in pain measures (p=0.033) and in general health status as assessed by SF-36® (Total Score, p=0.013). Importantly, none of the participants reported worsening in their general health status.

FIG. 1 shows a graph (1) displaying changes in pain as assessed by the Visual Analogue Scale (VAS) and in general health status as assessed by SF-36® Total Scores at the specified time intervals after initiation of placebo and agmatine sulfate treatments. Results, mean (±SEM, vertical lines) values are expressed as percent of baseline values. Asterisks indicate significant differences between the placebo- and agmatine sulfate-treated groups ($p \le 0.033$).

Based on the above described study and Example I, the preferred dose amount in humans is 1780 to 2670 mg per 24 hour period for long-term use in the diet. This range is based on administration to a human weighing 60 to 70 kg. It is understood by those with knowledge in the dietary supplement and nutraceutical art that the dose range selected will depend on the weight of human or animal. Of course, the amounts of each compound selected will depend on the weight of the mammal and the levels of cytoprotection that is needed. In humans, oral doses of up to 2.67 g/day of agmatine sulfate taken for over 2 years have not been associated with any adverse effects, and only mild, reversible diarrhea was observed with doses of up to 3.56 g/day.

The amount of the other traditional dietary ingredients to be used (including: minerals, fatty acids, amino acids and metabolites thereof, phytonutrients, vitamins and coenzymes) can be any amount that is considered safe for consumption and approved by the acceptable guidelines promulgated by the Food and Drug Administration and/or regulatory agencies such as the National Research Council's Recommended Dietary Allowances. One skilled in the art can adjust the dosage forms to achieve the desired therapeutic levels.

The preferred compositions of the present invention can be prepared and administered in a wide variety of oral dosage forms. It is obvious to those skilled in the art that the dosage forms may comprise a cytoprotective amount of agmatine consisted of nutraceutical acceptable salts thereof in combination with an effective amount of one or more dietary ingredients selected from the traditional group of minerals, fatty acids, amino acids and metabolites thereof, phytonutrients, vitamins and coenzymes.

For preparing the agmatine compositions, nutraceutical compatible carriers and excipients may be either solid or liquid. Solid form preparations include powders, tablets, capsules, soft gelatin capsules, controlled release capsules and tablets, lozenges and chewable preparations, and suspensions in an edible supporting matrix or foodstuff Liquid preparations include liquid suspensions and oral rehydration solutions. These preparations may contain, in addition to the active component, colorants, flavors, stabilizers, buffers, artificial and natural sweeteners, thickeners, solubilizing agents, dispersants, sorbants, glidants, disintegrants, and the like.

The nutraceutical compositions are preferably prepared in unit dosage form whereby the preparation is subdivided into unit doses containing appropriate quantities of the active component. The unit dosage form can be a packaged preparation containing discrete quantities of packaged tablets, lozenge, capsules, soft gelatin capsules, or controlled release capsules and tablets. Preferably, the controlled release period is suitable for once-daily (i.e., once within a 24 hour period) dosing of an effective dose of the nutraceutical compositions.

Optimally, the tablets, lozenge, capsules, soft gelatin capsules, or controlled release capsules and tablets may be coated with any pharmaceutically acceptable coating. The coatings may be applied for such purposes as product identification, printability of tablet, light protection, aesthetic appearance and patient compliance. Numerous pharmaceutically acceptable coating formulations have been developed by the pharmaceutical industry and are well known to the pharmaceutical scientist and are also commercially available.

This invention can be better understood from the examples which follow. However, one skilled in the art will readily appreciate that the examples described below are presented for illustration purposes only and are not intended to limit the scope of the invention of this application, which will be described more fully in the non-provisional application claims.

Example (I)

A study demonstrating for the first time that long-term dietary agmatine sulfate can be considered safe for human use and devoid of any side effects when ingested at the high daily dose range of 1.335-3.560 grams for duration of up to 2 years. This study is based on administration to humans weighing 60 to 70 kg.

Conductance:

Agmatine sulfate was manufactured according to international standards ISO 9001. It was encapsulated under cGMP (current Good Manufacturing Practice) conditions in gelatin-glycerin capsules as the sole active ingredient of the dietary supplement and the capsules packaged in properly labeled plastic container bottles.

The study was performed at Tel-Aviv Sourasky Medical Center, Israel and approved by the Institutional Review Board (Trial Number: 05-302) and by the Israel Ministry of Health National Review Board (Trial Number: 20050479), and conducted in accordance with the Helsinki guidelines under current Good Clinical Practice (cGCP) and the International Conference on Harmonization (ICH) guidelines. All procedures were performed after participants had read, understood and signed the informed consent form. Eligibility of consenting participants was determined after medical history recording, comprehensive clinical examination, and laboratory tests of blood samples to ensure inclusion/exclusion criteria.

Inclusion/Exclusion Criteria:

Inclusion Criteria: 1) Men and women 18-75 years of age, including also those diagnosed with spine skeletal pathologies causing nerve compression. 2) Women must be non-pregnant, non-lactating, or sterilized, or postmenopausal. 3) All participants must give a signed informed consent.

Exclusion Criteria: 1) Those with any significant clinical, medical or surgical condition, such as: cardiovascular, pulmonary, hepatic, renal, immune, endocrine, metabolic, digestive, malignancy, or allergic, and those with deviations from the normal laboratory test values. 2) Those with any neuromuscular diseases (other than spine skeletal pathologies causing nerve compression). 3) Those with any neurological diseases. 4) Those with any history of alcohol or substance abuse within the last 2 years. 5) Those with gastric ulcer history. 6) Those who took any experimental drug within 90 days prior to screening. 7) Women who are pregnant or breast feeding. 8) Those participating in other clinical trials.

Treatment and Regimen:

At the starting day of the study eligible participants began taking the supplement and had the option of receiving concomitantly any conventional treatment [e.g. drug treatment or physiotherapy] as needed for their welfare, and this was recorded throughout the duration of the study. However, any other experimental drug or dietary supplement was disallowed.

TABLE 1

Detailed treatment regimen and number of participants in the consecutive cohorts.

| Cohort | No. of participants | Agmatine Sulfate Treatment Regimen |
|---|---|---|
| $1^{st}$ Cohort | 5 | 1 capsule 3 times daily (1.335 g/day) for 10 days |
| $2^{nd}$ Cohort | 5 | 2 capsules 3 times daily (2.670 g/day) for 10 days |
| $3^{rd}$ Cohort | 12 | 8 daily capsules (2 in the morning, 3 at noontime and 3 in the evening) (3.560 g/day) for 10 days |
| $4^{th}$ Cohort | 12 | 8 daily capsules (2 in the morning, 3 at noontime and 3 in the evening) (3.560 g/day) for 21 days |
| Post Trial Cohorts | | |
| $5^{th}$ Cohort | 8 | 2 capsules 3 times daily (3.560 g/day) for 90 days |
| $6^{th}$ Cohort | 6 | 2 capsules 3 times daily (2.670 g/day) for 720 days |

Table 1 details the escalating doses and regimens taken by the consecutive cohorts. Following screening to ensure inclusion/exclusion criteria, 48 men and women, 28 to 70 years old were recruited consecutively to the study after they gave a signed informed consent. Eligible participants took 3 times a day, after meals (morning, noontime and evening), the specified daily dose of agmatine sulfate capsules. Each capsule contained 445 mg of agmatine sulfate (Table 1).

Methods:

Before beginning and within 5 days after termination—and before the next cohort began taking the supplement—all cohort participants underwent thorough clinical evaluation and routine laboratory tests of blood samples to ascertain normal function of the cardiovascular, hepatic, renal, immune and metabolic systems.

Figure 2:
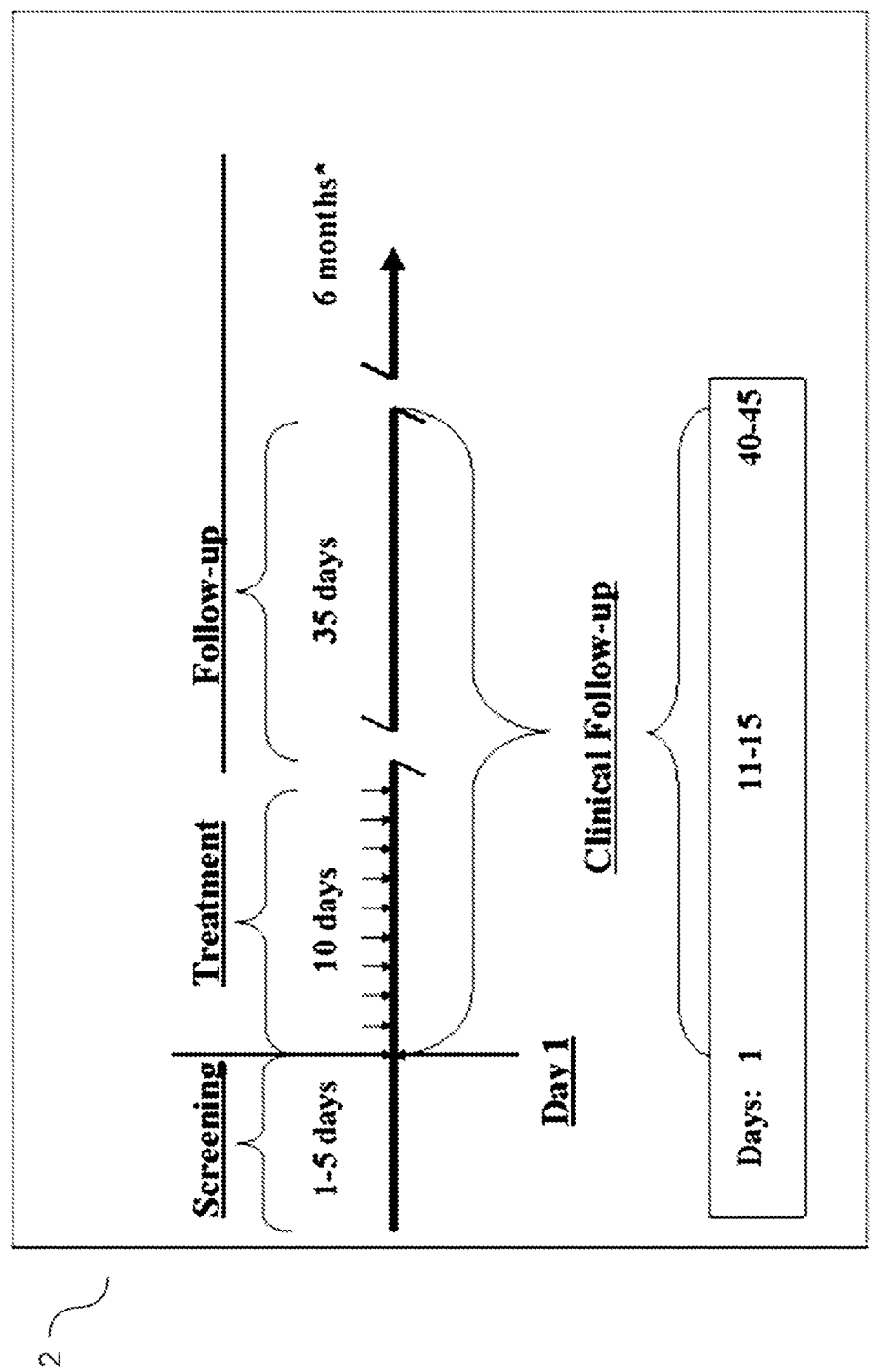
FIG. 2 illustrates a Study Flow Chart in accordance with the present invention.

Follow-Up:

In-person evaluations were performed at: 11-15 days, 22-25 days, 40-45 days after treatment starting day (day 1), and then telephone interview evaluations every 3-6 months for the duration of the trial. The flow chart (2) outlined in FIG. 2 illustrates the treatment and follow-up schedules as exemplified for a 10-day cohort. In addition, participants received a "participant diary" for self recording of any outstanding health related events during the treatment interval.

FIG. 2 shows a Study Flow Chart (2) (example for a 10-day cohort). *Follow-up by telephone interview evaluation.

Data Handling and Analysis:

For the sake of privacy, all records and data were identified only by participants' code number. All "source data" documents were stored in individual patient files and kept at the clinical center by the principal investigator and copies are kept with the study sponsor. Safety Evaluation—was performed by analyses of clinical examinations and laboratory blood tests, and evaluation of the participant diaries. Tolerability—was assessed based on the number of participants who failed to complete the study of their free will or as a result of adverse effects, and on the time to withdrawal. Participants who prematurely discontinued remained under follow-up for the duration of the study. The results were tabulated and presented by descriptive statistics including mean and range values.

Results
Safety and Tolerability

The study population descriptors are summarized in Table 2. Participants in the study were 48 men and women, 28-70 years of age. Under the studied regimens, dietary agmatine sulfate was found to be safe by all measures used. Clinical examinations and laboratory analyses of blood samples revealed no abnormality in any parameter studied in all participants of the trial.

Side Effects

Only 3 participants reported mild-to-moderate side effects (Table 2). One participant of the $3^{rd}$ cohort (3.560 g/day, for 10 days) and 2 of the $4^{th}$ cohort (3.560 g/day, for 21 days) reported having discomfort as a result of mild-to-moderate diarrhea and nausea during treatment that began at 2 to 3 days and disappeared within 2 day after treatment cessation. One of the latter 2 belonging to the $4^{th}$ cohort discontinued the study 10 days after starting the treatment as a result of the indicated adverse effect. The other one chose to discontinue the study after 7 days for personal reasons not related to the reported adverse effects. Both participants who discontinued remained under follow-up for the study duration. None of the above 3 participants had any other abnormality. In sum, only 2 participants failed to complete the study, one as a result of free will discontinuation and the other as a result of mild-to-moderate adverse effects (Table 2).

agmatine sulfate 5.3 g/l, while controls (n=10) drank regular sterile drinking-water for 95 days. Drinking-water containing agmatine sulfate have bitter taste.

Measurements and Analysis:

Animal body weight and systolic blood pressure (SBP) as measured by tail-cuff plethysmography (IITC Life Science, Woodland Hills, Calif.) were measured at the starting day of the experiment (day 1) and at various intervals thereafter. General behavior, fur appearance and feces appearance were also assessed. Water consumption was measured daily. After 95 days, 5 animals of each group were deeply anesthetized (750 mg/kg sodium pentobarbital, intraperitoneal) and the stomach, kidney, heart and liver removed for gross inspection. The stomach was inspected for appearance of ulcers. The rest of the animals, in both the control and experimental groups, were all maintained on regular diet (without agmatine sulfate in the drinking-water) for additional 20 days and then killed (on the $115^{th}$ day). Results were evaluated by analysis of variance (ANOVA) procedure. Differences were analyzed by 2-tailed t-test and values of p≤0.05 were considered statistical significant. For data normalization, differences were expressed as percent change of day 1 values.

Results

The daily consumption of agmatine sulfate was calculated using the average value of 27.15 ml of daily water consumption observed in the agmatine sulfate-treated group

TABLE 2

Patient demographic characteristics, clinical status and adverse effects.

| Category | $1^{st}$ Cohort | $2^{nd}$ Cohort | $3^{rd}$ Cohort | $4^{th}$ Cohort | $5^{th}$ Cohort | $6^{th}$ Cohort |
|---|---|---|---|---|---|---|
| Number of Participants (n): | 5. | 5. | 12. | 12. | 9. | 5. |
| Males - | 3 | 1 | 7 | 8 | 4 | 3 |
| Females - | 2 | 4 | 5 | 4 | 4 | 3 |
| Age (years): | | | | | | |
| Mean - | 54.2 | 52.2 | 52.3 | 52.6 | 41.4 | 42.3 |
| Range - | 31-63 | 40-59 | 28-70 | 36-64 | 30-61 | 30-61 |
| Number of Participants with Skeletal Pathologies: | 5 | 5 | 12 | 11 | 2 | 1 |
| Concomitant Treatment (no. of participants): | | | | | | |
| Medication (NSAID) - | 3 | 1 | | 1 | 3 | 2 |
| Physiotherapy - | 2 | | | | 1 | 1 |
| Adverse Effects (no. of participants): | | | | | | |
| Nausea and Diarrhea - | | | 1 | 2 | | |
| Discontinuations - Due to Adverse Effects: | | | | 1 | | |
| Free Will Discontinuations: | | | | 1 | | |

Example (II)

A study demonstrating for the first time that sub-chronic intake of high dose agmatine sulfate in the drinking water has no general toxic or unwanted effect on laboratory rats.

Methods

Animals and Treatment:

The experiment was performed at Assaf Harofeh Medical Center, Israel, according to the Institutional Animal Care and Use Committee approved protocol. Three-month-old male Wistar rats (Harlan, Israel) weighing 250±20 g were caged individually under standard vivarium conditions of temperature (22±2° C.), humidity (55-75%) and light (12 h light-dark cycle) with a free supply of food and water. Experimental animals (n=10) drank sterile water containing over the 95 day treatment period (Table 3) Drinking-water contained 5.3 g/l agmatine sulfate; thus, rats consumed on the average 143.9 mg agmatine sulfate per day, or 568.8 mg/kg when calculated per kg body weight [assuming an average body weight of 253 g (Table 3)].

Table 3 summarizes the main measurements. Experimental animals showed reduction in volume of water intake and reduced weight gain with actual weight loss during the first 3 weeks of treatment. These changes were apparent immediately after day 1 and persisted for the duration of agmatine sulfate treatment. Animals switched to regular drinking water after 95 days demonstrated recovery in weight gain within 20 days (Table 3). The cause of these changes, therefore, was most probably the bitter taste of the drinking-water containing agmatine sulfate. Giving agmatine sulfate in the animal feed (chow pellets) should solve the weight loss effect.

the facial nerve was crushed unilaterally while the other 7 were left unoperated. Surgery was performed under halothane anesthesia (1.5% in 100% $O_2$) and the facial nerve

TABLE 3

Changes in body weight, daily drinking volume and systolic blood pressure of rats at the beginning (day 1), and during (21 and 95 days) of drinking agmatine sulfate containing water, and at 20 days after treatment (day 115), as compared to controls.
Mean values are also expressed as percent change of day 1.

| Group (Animal No.) | Body Weight (g) | | | | Daily Drinking (ml) | | | | Blood Pressure (mm Hg) | | | |
|---|---|---|---|---|---|---|---|---|---|---|---|---|
| | Day 1 | Day 21 | Day 95 | Day 115 | Day 1 | Day 21 | Day 95 | Day 115 | Day 1 | Day 21 | Day 95 | Day 115 |
| Control | | | | | | | | | | | | |
| 1 | 250 | 245 | 260 | | 35.1 | 35.8 | 36.2 | | 101.0 | 104.0 | 100.0 | |
| 2 | 235 | 240 | 255 | | 34.0 | 33.5 | 36.4 | | 108.0 | 110.0 | 107.0 | |
| 3 | 240 | 245 | 258 | | 35.6 | 36.8 | 31.7 | | 100.0 | 100.0 | 104.0 | |
| 4 | 250 | 250 | 266 | | 33.5 | 31.0 | 33.3 | | 101.0 | 100.0 | 101.0 | |
| 5 | 255 | 259 | 270 | | 35.0 | 34.3 | 35.8 | | 102.0 | 105.0 | 105.0 | |
| 6 | 257 | 261 | 275 | 278 | 35.6 | 35.4 | 36.0 | 37.4 | 110.0 | 107.0 | 110.0 | 110.0 |
| 7 | 248 | 253 | 267 | 269 | 34.8 | 35.7 | 36.5 | 31.0 | 107.0 | 109.0 | 104.0 | 105.0 |
| 8 | 260 | 260 | 272 | 277 | 35.7 | 36.0 | 36.7 | 36.2 | 103.0 | 105.0 | 106.0 | 102.0 |
| 9 | 252 | 258 | 275 | 279 | 34.6 | 32.5 | 32.5 | 35.0 | 101.0 | 100.0 | 102.0 | 100.0 |
| 10 | 245 | 251 | 266 | 269 | 34.5 | 35.2 | 33.9 | 35.3 | 104.0 | 103.0 | 105.0 | 104.0 |
| Mean ± SEM | 249.2 ± 0.8 | **252.2\* ±  0.8** | **266.4\* ± 0.7** | **274.4\* ± 1.2** | 34.8 ± 0.1 | 34.6 ± 0.2 | 34.9 ± 0.2 | 35.0 ± 0.6 | 103.7 ± 0.4 | 104.3 ± 0.4 | 104.4 ± 0.3 | 104.2 ± 0.9 |
| (% Change) | (100) | (101.2) | (106.9) | (108.4) | (100) | (99.4) | (100.3) | (99.7) | (100) | (100.6) | (1003) | (101.0) |
| Agmatine Sulfate | | | | | | | | | | | | |
| 1 | 250 | 255 | 265 | | 35.5 | 21.4 | 25.6 | | 99.0 | 97.0 | 95.0 | |
| 2 | 250 | 245 | 257 | | 34.8 | 25.3 | 28.7 | | 100.0 | 95.0 | 97.0 | |
| 3 | 265 | 260 | 273 | | 35.6 | 25.1 | 30.0 | | 105.0 | 100.0 | 101.0 | |
| 4 | 255 | 245 | 257 | | 34.7 | 25.0 | 27.7 | | 112.0 | 109.0 | 110.0 | |
| 5 | 257 | 227 | 253 | | 33.4 | 24.1 | 29.6 | | 115.0 | 115.0 | 112.0 | |
| 6 | 247 | 242 | 251 | 256 | 35.0 | 25.5 | 30.3 | 34.5 | 110.0 | 103.0 | 105.0 | 108.0 |
| 7 | 245 | 245 | 255 | 261 | 33.8 | 26.4 | 30.0 | 35.3 | 109.0 | 107.0 | 106.0 | 107.0 |
| 8 | 252 | 250 | 255 | 259 | 35.6 | 24.9 | 28.4 | 34.9 | 105.0 | 103.0 | 101.0 | 104.0 |
| 9 | 260 | 255 | 263 | 267 | 34.5 | 27.0 | 31.3 | 35.0 | 102.0 | 100.0 | 99.0 | 103.0 |
| 10 | 253 | 249 | 260 | 264 | 35.0 | 26.7 | 30.6 | 34.8 | 107.0 | 106.0 | 105.0 | 107.0 |
| Mean ± SEM | 253.4 ± 0.7 | <u>247.3\* ± 1.0</u> | **258.9\* ± 0.7** | **261.4\* ± 1.1** | 34.8 ± 0.1 | <u>25.1\* ± 0.2</u> | <u>29.2\* ± 0.2</u> | 34.9 ± 0.1 | 106.4 ± 0.6 | <u>103.5\* ± 0.7</u> | <u>103.1\* ± 0.6</u> | 105.8 ± 0.5 |
| (% Change) | (100) | <u>(97.6)</u> | (102.2) | (103.9) | (100) | <u>(72.1)</u> | <u>(83.9)</u> | (99.7) | (100) | <u>(97.3)</u> | <u>(96.9)</u> | (99.1) |

\*= p < 0.05, as compared to day 1. Significantly increased values are in bold; significantly reduced values are underlined.

Systolic blood pressure showed a slight, but significant reduction in agmatine sulfate-treated rats confirming previous reports and this recovered when examined 20 days after treatment cessation (Table 3). No other significant changes were observed. Thus, general cage behavior, fur appearance and feces appearance were all normal and inspection of main internal organs did not reveal any gross changes. Importantly, no stomach ulcers were observed.

Example (III)

A study demonstrating for the first time that intake of dietary agmatine sulfate in the drinking water prior to nerve injury can significantly accelerate subsequent functional recovery in laboratory rats.

Methods

Animals and Treatment:

The experiment was performed at Assaf Harofeh Medical Center, Israel, with 4-month-old male Wistar rats (Harlan, Israel) kept under standard conditions in the Institute's vivarium according to the Institutional Animal Care and Use Committee approved protocols (see Example II above). Twenty four rats were divided into 2 groups of 14 animals each, one group drank sterile water containing agmatine sulfate 5.3 g/l, while the other drank regular sterile drinking-water for a period of 21 days. On day 21 both groups were switched to drink regular tap water. In 7 rats from each group was crushed unilaterally at the stylomastoid foramen for 20 seconds with a jeweler's forceps under the operating microscope.

Measurements and Analysis:

Transection of the facial nerve, which innervates the upper and lower lips results in paralysis of the vibrissae (whiskers) on the operated side. Functional recovery was assessed by evaluation of vibrissae movement for up to 14 days postoperatively using the following arbitrary scale of 0 to 4: 0, complete paralysis with vibrissae flattened backwardly; —1, slight vibrating motion; —2, mild proximal vibrating motion; —3 moderate motion of vibrissae and lips; 4, full motion of lower face and vibrissae. Results were evaluated by analysis of variance (ANOVA) procedure followed by Bonferroni post hoc testing and differences considered significant at p<0.05.

Results

Figure 3:
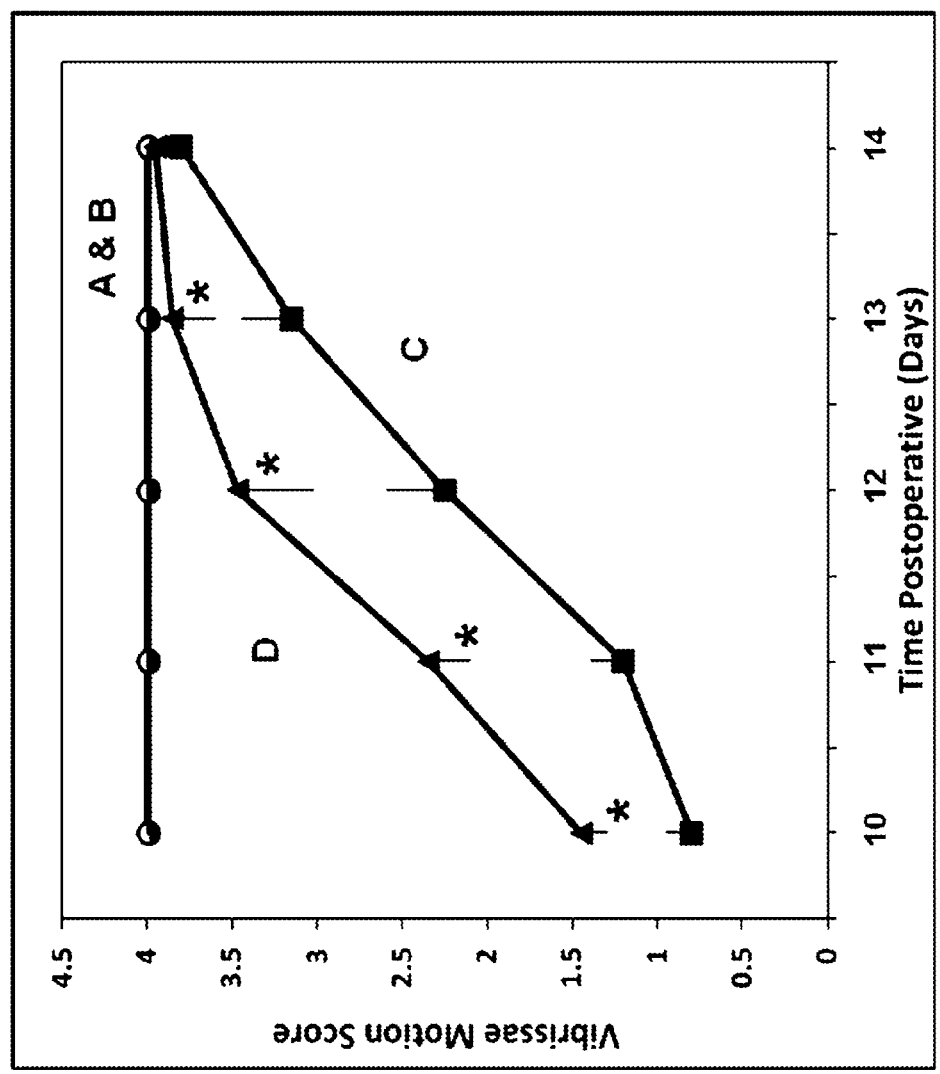
FIG. 3 shows a graph displaying changes in vibrissae movement in accordance with the present invention

The graph (3) shown in FIG. 3 demonstrates the time course of vibrissae functional recovery after nerve crush injury. As observed in group C, the first signs of recovery in this experimental model are normally observed at 10-11 days, 50% by day 12 and full recovery is achieved by 14 days after injury. Consumption of agmatine sulfate for 21 days in the drinking water prior to a facial nerve crush (group D), resulted in a significantly accelerated recovery of vibrissae movement. Prior agmatine consumption resulted in 181.2% increase in vibrissae motion as compared to controls (group C) already by day 10 after injury, with nearly full recovery being achieved by day 12 as compared to day 14 in controls, as shown in graph (3) in FIG. 3.

The graph (3) displays changes in vibrissae movement at days 10-14 ipsilateral to a unilateral facial nerve crush in the following treatment groups: A. Regular sterile drinking-water and unoperated (controls, open circle). B. sterile water containing agmatine and unoperated (controls, semisolid circle). C. Regular sterile drinking-water and nerve crush (solid square). D. sterile water containing agmatine and nerve crush (solid triangle). Results are the mean (±SEM, vertical lines) values of 7 animals. *=p<0.001 comparing group C to group D values.

Example (IV)

Encapsulation by filling 445 mg agmatine sulfate crystalline powder into hard gelatin-glycerin capsules size 0, without the use of excipients. Proportionally larger quantities are filled into larger size capsules.

Example (V)

Encapsulation using hard shell gelatin-glycerin capsules is prepared using the following formulation: A mixture of 445 mg/capsule agmatine sulfate crystalline powder with or without magnesium stearate as lubricant 0.5%, silicon dioxide as glidant 0.5%, or cellulose (e.g., croscarmellose) as disintegrant 2.0%, is filled into hard gelatin-glycerin capsules size 0. Proportionally larger quantities are filled into larger size capsules.

Example (VI)

Encapsulation using hard shell gelatin-glycerin capsules is prepared using the following formulation: A mixture of 385 mg/capsule agmatine sulfate crystalline powder and 60 mg magnesium chloride, with or without magnesium stearate as lubricant 0.5%, silicon dioxide as glidant 0.5%, or cellulose (e.g., croscarmellose) as disintegrant 2.0%, is filled into hard gelatin-glycerin capsules size 0. Proportionally larger quantities are filled into larger size capsules.

Example (VII)

Encapsulation using hard shell gelatin-glycerin capsules is prepared using the following formulation: A mixture of 445 mg/capsule agmatine sulfate crystalline powder and 9 mcg sodium selenite ($Na_2SeO_3$) with or without magnesium stearate as lubricant 0.5%, silicon dioxide as glidant 0.5%, or cellulose (e.g., croscarmellose) as disintegrant 2.0%, is filled into hard gelatin-glycerin capsules size 0. Proportionally larger quantities are filled into larger size capsules.

Various other examples of compositions and modifications or adaptations thereof can be devised by a person skilled in the art after reading the foregoing preferred embodiments without departing from the spirit and scope of the invention. All such further examples, modifications and adaptations are included within the scope of the invention.

It will be appreciated by those versed in the art that the present invention makes available novel and useful nutraceutical compositions containing agmatine and nutraceutical acceptable salts thereof, which have cytoprotective effects in several administration forms. Also, it will be understood by those with knowledge in the dietary supplement and nutraceutical art, that many embodiments of this invention may be made without departing from the spirit and scope of the invention, and the invention is not to be construed as limited, as it embraces all equivalents therein.

What is claimed is:

1. A method of promoting the recovery of traumatized cells by prophylactically cytoprotecting healthy cells, the method comprising the following agmatine regimen:
    administering a dietary supplement that includes an agmatine salt to a human who is asymptomatic for any neuropathy or neurological disorders, comprising:
    an amount of the agmatine salt in a megadose range of 1780 milligrams per 70 kilograms body weight per day to 3560 milligrams per 60 kilograms body weight per day;
    continuing the administration of said dietary supplement on a daily basis, but for at least approximately 21 days;
    discontinuing the administration of said dietary supplement when said human experiences a neurological trauma after approximately 21 days of administration of said dietary supplement; and,
    wherein said traumatized cells correspond to said healthy cells after said healthy cells experience a trauma;
    whereby said agmatine regimen promotes recovery of traumatized cells with the ability to recover from trauma more quickly than said traumatized cells would otherwise be able to do.

2. The method of claim 1, wherein the dietary supplement further comprises
    one or more dietary ingredients selected from the group consisting of minerals, fatty acids, metabolites, amino acids, phytonutrients, vitamins, and coenzymes.

3. The method of claim 2, wherein the dietary supplement further comprises
    an excipient
    wherein said excipient enables consumption of said dietary supplement.

4. The method of claim 1, wherein the dietary supplement further comprises
    an excipient
    wherein said excipient enables consumption of said dietary supplement.

5. The method of claim 1, wherein the dietary supplement further comprises
    a medical food portion;
    wherein said dietary supplement is incorporated into said medical food portion.

6. The method of claim 5, wherein the dietary supplement further comprises
    one or more dietary ingredients selected from the group consisting of minerals, fatty acids, metabolites, amino acids, phytonutrients, vitamins, and coenzymes.

7. The method of claim 1 further comprising
    providing a processed food comprising
    the dietary supplement and
    a food portion;
    wherein said dietary supplement is incorporated into said food portion.

8. The method of claim 7, wherein said food portion is fortified with one or more health promoting ingredients.

9. The method of claim 8, wherein said food portion is selected from the group consisting of cereals and fermented dairy products.

10. The method of claim 1 further comprising
    providing a processed beverage comprising
    the dietary supplement and
    a beverage portion;
    wherein said dietary supplement is incorporated into said beverage portion.

11. The method of claim 10, wherein said beverage portion is fortified with one or more health promoting ingredients.

12. The method of claim 11, wherein said beverage portion is selected from the group consisting of tea, juice, water, and alcoholic beverages.

13. The method of claim 1, wherein the promoting of the recovery of traumatized cells is further characterized by promoting accelerated recovery of non-neuronal tissues adjacent to or affected by neuronal tissues.

14. A method of promoting the recovery of traumatized cells by prophylactically cytoprotecting healthy cells, the method comprising the following agmatine regimen:

administering a dietary supplement that includes an agmatine salt to an animal that is asymptomatic for any neuropathy or neurological disorders, comprising:

an amount of the agmatine salt in a megadose range of 10 milligrams per kilograms body weight per day to 500 milligrams per kilograms body weight per day;

continuing the administration of said dietary supplement on a daily basis, but for at least approximately 21 days; and, discontinuing the administration of said dietary supplement when said animal experiences a trauma after at least approximately 21 days of administration of said dietary supplement;

wherein said traumatized cells correspond to said healthy cells after said healthy cells experience a trauma;

whereby said agmatine regimen promotes recovery of traumatized cells with the ability to recover from trauma more quickly than said traumatized cells would otherwise be able to do.

15. The method of claim 14, wherein said animals are selected from a group consisting of rats and mice, and wherein said effective dose range amount of agmatine for said rats and mice comprises 200 milligrams per kilogram body weight per day to 500 milligrams per kilogram body weight per day of the agmatine salt.

16. The method of claim 14, wherein said animals are dogs, and wherein said effective dose range amount of agmatine for said dogs comprises 20 milligrams per kilogram body weight per day to 80 milligrams per kilogram body weight per day of the agmatine salt.

17. The method of claim 14, wherein said animals are horses, and wherein said effective dose range amount of agmatine for said horses comprises 10 milligrams per kilogram body weight per day to 40 milligrams per kilogram body weight per day of the agmatine salt.

18. The method of claim 14 further comprising
providing a processed food comprising
the dietary supplement and
an animal feed,
wherein said dietary supplement is incorporated into said animal feed.

19. The method of claim 14, wherein the promoting of the recovery of traumatized cells is further characterized by promoting accelerated recovery of non-neuronal tissues adjacent to or affected by neuronal tissues.

* * * * *